US008916398B2

(12) United States Patent
Li et al.

(10) Patent No.: US 8,916,398 B2
(45) Date of Patent: Dec. 23, 2014

(54) ENCAPSULATED STRUCTURE OF LIGHT-EMITTING DEVICE, ENCAPSULATING PROCESS THEREOF AND DISPLAY DEVICE COMPRISING ENCAPSULATED STRUCTURE

(71) Applicant: Boe Technology Group Co., Ltd., Beijing (CN)

(72) Inventors: Na Li, Beijing (CN); Joo Hyeon Lee, Beijing (CN); Pil Seok Kim, Beijing (CN)

(73) Assignee: Boe Technology Group Co., Ltd., Beijing (CN)

( * ) Notice: Subject to any disclaimer, the term of this patent is extended or adjusted under 35 U.S.C. 154(b) by 0 days.

(21) Appl. No.: 14/039,896

(22) Filed: Sep. 27, 2013

(65) Prior Publication Data

US 2014/0091290 A1 Apr. 3, 2014

(30) Foreign Application Priority Data

Sep. 28, 2012 (CN) .......................... 2012 1 0369893

(51) Int. Cl.
*H01L 51/54* (2006.01)
*H01L 51/52* (2006.01)
*H01L 33/52* (2010.01)
*C07C 249/02* (2006.01)
*H01L 51/56* (2006.01)

(52) U.S. Cl.
CPC ............ *H01L 51/5253* (2013.01); *H01L 33/52* (2013.01); *C07C 249/02* (2013.01); *H01L 51/56* (2013.01)
USPC .......................................... 438/26; 257/788

(58) Field of Classification Search
CPC ..... H01L 33/52; H01L 33/56; H01L 51/5253; H01L 51/56

USPC .............................................. 257/788; 438/26
See application file for complete search history.

(56) References Cited

U.S. PATENT DOCUMENTS

| 3,079,220 | A | * | 2/1963 | Boies et al. ...................... 422/19 |
| 8,729,715 | B2 | * | 5/2014 | Iwashige et al. ............... 257/788 |
| 2002/0193551 | A1 | * | 12/2002 | Pei .................................. 528/86 |
| 2003/0013843 | A1 | * | 1/2003 | Pei ................................. 528/422 |
| 2011/0009549 | A1 | * | 1/2011 | Zhou ............................. 524/291 |

FOREIGN PATENT DOCUMENTS

JP 58128756 A * 8/1983
JP 2012031091 A * 2/2012

OTHER PUBLICATIONS

First Chinese Office Action Appln. No. 2012103698938; Issue Date Sep. 26, 2014.

* cited by examiner

*Primary Examiner* — Allan R Wilson
(74) *Attorney, Agent, or Firm* — Ladas & Parry LLP

(57) ABSTRACT

An encapsulated structure of a light-emitting device, an encapsulating process thereof, and a display device comprising said encapsulated structure. The encapsulated structure of the light-emitting device comprises: a light-emitting device; and a protective layer of a quaternary ammonium salt formed on a top electrode of the light-emitting device, the quaternary ammonium salt having the following structure:

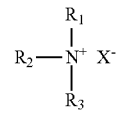

wherein the anion $X^-$ is $Cl^-$, $Br^-$, $I^-$ or $NO_3^-$; and the substituents $R_1$, $R_2$, and $R_3$ are the same or different.

11 Claims, 2 Drawing Sheets

ENCAPSULATED STRUCTURE OF LIGHT-EMITTING DEVICE, ENCAPSULATING PROCESS THEREOF AND DISPLAY DEVICE COMPRISING ENCAPSULATED STRUCTURE

FIELD OF INVENTION

The invention relates to an encapsulated structure of a light-emitting device, an encapsulating process thereof and a display device comprising the encapsulated structure.

BACKGROUND ARTS

Small molecule organic electroluminescence device (OLED) and Polymer organic electroluminescence device (PLED) have the advantages of active light-emitting, high brightness, full-color display, low driving voltage, low device thickness, flexible display ability, and simpler manufacturing process as compared to the liquid crystal display (LCD) device and plasma display device (PDP), and the like, and have a promising application in large screen flat panel displays and flexible displays.

According to the differences in the organic film materials of the carrier transport layer and the light-emitting layer used in the components, the organic electroluminescence device can be divided into two different classes. One is small molecule-based organic LEDs, briefly OLEDs, which use organic dyes and pigments as the light-emitting materials, wherein a reprehensive example of small molecule light-emitting material is Alq (8-hydroxyquinoline aluminum). The other is polymer-based LEDs, briefly PLED, which use conjugated polymers as the light-emitting materials, wherein a reprehensive example of polymer light-emitting material is PPV (polyphenylene vinylene and derivatives thereof). Organic electroluminescence device is a current type semiconductor light-emitting device based on an organic material. Its structure is typically obtained by forming a light-emitting layer made of an organic light-emitting material with a thickness of some dozens of nanometers on an ITO glass, followed by disposing a layer of low work function metal electrode above the light-emitting layer. When a voltage is applied to the electrode, light radiation occurs in the light-emitting layer.

The organic light-emitting materials in OLED/PLED are very sensitive to water vapor and oxygen gas, and very small amount of water vapor and oxygen gas can damage the organic light-emitting materials and make the light-emitting performance of the device deteriorate. Therefore, it is a very important issue to be solved in the encapsulation of organic electroluminescence device how to reduce the permeation of water vapor and oxygen gas into the encapsulating material of the device and eliminate the water vapor and oxygen gas inside the device. In order to ensure that the device has a service life satisfactory for commercial applications, the permeation rate of the water vapor and oxygen gas into the encapsulated structure and materials of the device should be lower than $10^{-6}$ g/m$^2$/day.

Figure 1:
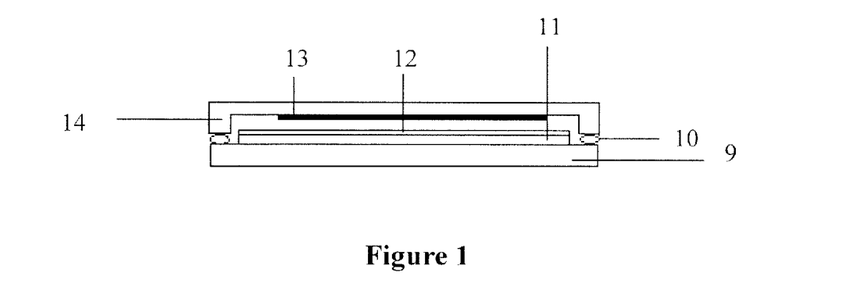
FIG. 1 is a schematic diagram of the components of the encapsulated structure of the organic electroluminescence device in the prior art.
Figure 2:
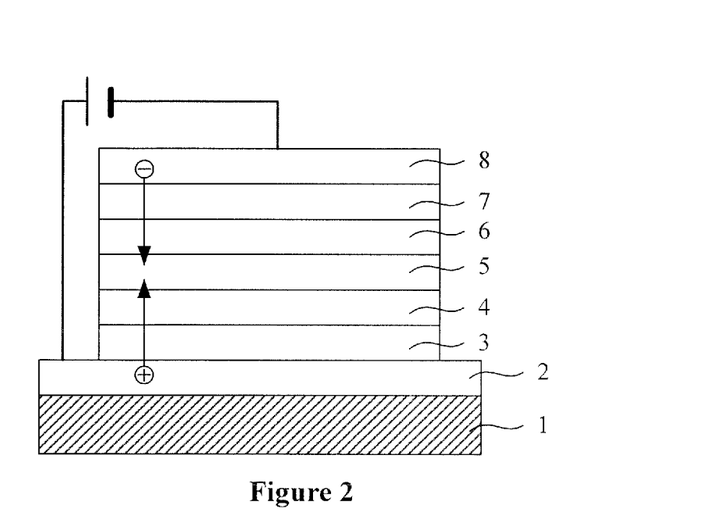
FIG. 2 is a schematic diagram of the structure of the organic layer in the organic electroluminescence device.

The structure of a bottom emission rigid OLED/PLED device which is conventionally encapsulated is shown in FIG. 1. An organic layer 11 and a metal electrode 12 are vapor deposited onto an ITO glass 9, respectively, and an encapsulating cover 14 attached with a drying slide 13 and a frame sealant 10 is encapsulated onto the ITO glass 9. The organic layer 11 is the light-emitting functional layer which has a structure as shown in FIG. 2, and it may comprise a hole injection layer (HIL) 3, a hole transporting layer (HTL) 4, an organic light-emitting layer (EML) 5, an electron transporting layer (ETL) 6, and an electron injection layer (EIL) 7.

The conventional encapsulating process has such disadvantages as complicated operational procedure, long curing time and high cost, and the like Moreover, because the drying slide 13 is not transparent, the conventional encapsulating process is only applicable to OLED bottom emission devices but not applicable to top emission devices.

SUMMARY OF INVENTION

An embodiment of the invention provides an encapsulated structure of a light-emitting device comprising,
a light-emitting device;
a protective layer of a quaternary ammonium salt formed on a top electrode of the light-emitting device, wherein the quaternary ammonium salt has the following structure:

wherein the anion $X^-$ is $Cl^-$, $Br^-$, $I^-$ or $NO_3^-$; and
the substituents $R_1$, $R_2$, $R_3$ are the same or different.

For example, the substituent $R_1$ is selected from the group consisting of substituted alkyl groups having more than 5 carbon atoms, unsubstituted alkyl groups having more than 5 carbon atoms, alkoxyl groups having more than 5 carbon atoms and aralkyl groups having more than 11 carbon atoms.

The substituent $R_2$ is selected from the group consisting of substituted alkyl groups having more than 5 carbon atoms, unsubstituted alkyl groups having more than 5 carbon atoms, alkoxyl groups having more than 5 carbon atoms and aralkyl groups having more than 11 carbon atoms.

The substituent $R_3$ is selected from the group consisting of substituted alkyl groups having more than 5 carbon atoms, unsubstituted alkyl groups having more than 5 carbon atoms, alkoxyl groups having more than 5 carbon atoms and aralkyl groups having more than 11 carbon atoms.

The substituent $R_1$, $R_2$, and $R_3$ are independently selected from the group consisting of substituted alkyl groups having 5-20 carbon atoms, unsubstituted alkyl groups having 5-20 carbon atoms, alkoxyl groups having 5-20 carbon atoms and aralkyl groups having 11-26 carbon atoms.

An embodiment of the invention further provides a display device comprising the encapsulated structure of the light-emitting device as described above.

An embodiment of the invention further provides a process for encapsulating a light-emitting device to form the encapsulated structure of the light-emitting device as described above comprising,
preparing a light-emitting device to be encapsulated; and
forming a protective layer of a quaternary ammonium salt on a top electrode of the light-emitting device, the quaternary ammonium salt having the following structure:

wherein the anion $X^-$ is $Cl^-$, $Br^-$, $I^-$ or $NO_3^-$; and
the substituents $R_1$, $R_2$, and $R_3$ are the same or different.

DETAILED DESCRIPTION OF INVENTION

In order to make the technical problem to be solved, the technical solutions and advantages of the invention more clear, detailed descriptions are presented below in conjunction with figures and specific embodiments.

The process for encapsulating an organic electroluminescence device in the prior art has such disadvantages as complicated operational procedure, long curing time, and high cost, and the like, and is only applicable to OLED bottom emission devices but not applicable to top emission devices. In order to solve these issues, an embodiment of the invention provides an encapsulated structure of a light-emitting device, an encapsulating process thereof, and a display device comprising the encapsulated structure. The encapsulated structure allows for encapsulating an OLED top emission device, and the encapsulating process is simple and has the advantages of short curing time, low cost, and good barrier property to oxygen and moisture.

The directions represented by the term "above" or "below" as mentioned in the embodiments of the invention may indicate either direct or indirect contact.

The light-emitting device according to the embodiment of the invention will be described in a form of a top emission organic electroluminescence device. The organic electroluminescence device has a structure typically comprising a substrate, on the surface of which an anode layer, an organic light-emitting layer, and a cathode layer (that is, the cathode or top electrode) are formed successively from bottom to top. The organic electroluminescence device may further comprise one or more of hole injection layers and one or more of hole transporting layers formed successively between the anode layer and the organic light-emitting layer, as well as one or more of electron transporting layers and one or more of electron injection layers formed successively between the organic light-emitting layer and the cathode layer.

An embodiment of the invention provides an encapsulated structure of a light-emitting device comprising,
a light-emitting device;
a protective layer of a quaternary ammonium salt formed on a top electrode of the light-emitting device, the quaternary ammonium salt having the following structure:

wherein the anion $X^-$ is $Cl^-$, $Br^-$, $I^-$ or $NO_3^-$; and
the substituents $R_1$, $R_2$, $R_3$ are the same or different, and may be independently selected from the group consisting of substituted alkyl groups having more than 5 carbon atoms, unsubstituted alkyl groups having more than 5 carbon atoms, alkoxyl groups having more than 5 carbon atoms and aralkyl groups having more than 11 carbon atoms. Furthermore, the encapsulated structure further comprises:
an encapsulating cover disposed above the protective layer of the quaternary ammonium salt;
the light-emitting device further comprises a substrate, wherein the encapsulating cover is fixed to the substrate of the light-emitting device with a frame sealant.

Furthermore, the protective layer of the quaternary ammonium salt has a light transmittance of no less than 70%. The protective layer of the quaternary ammonium salt has a thickness of 1 to 100 nm.

For example, the light-emitting device is a top emission light-emitting device, and the encapsulating cover is transparent.

The protective layer of the quaternary ammonium salt according to the embodiment of the invention may comprise a single layer or multiple layers. Moreover, the quaternary ammonium salt material in the single layer or in each of multiple layers may be a single quaternary ammonium salt material or a composite material composed of multiple quaternary ammonium salt materials. As an example, a single layer made of a single material will be described below.

In an embodiment of the invention, a layer of quaternary ammonium salt is formed on the top electrode of the light-emitting device as a device protective layer. The protective layer of the quaternary ammonium salt can form a compact self-assembled film on the metal cathode of the light-emitting device. The anion at one side of the film can bind tightly to the metal via electrostatic force, and the hydrophobic moiety at the other side can block the invasion of water and oxygen, and protect the device from any damage caused by friction. Therefore, the embodiment of the invention overcomes the disadvantages of the conventional encapsulating process including complicated operational procedure, long curing time, and high cost, and the like, has the advantages of simple operation, short curing time, low cost, and good barrier property to oxygen and moisture, and the like, and allows the encapsulation of an OLED top emission device. The process for encapsulating a light-emitting device according to an embodiment of the invention is applicable to both top emission devices and bottom emission devices. For top emission devices, a layer of quaternary ammonium salt with high transmittance in the visible region is formed on the top electrode of the light-emitting device as the device protective layer, upon which a transparent encapsulating cover with a frame sealant attached is pressed. Therefore, the present disclosure addresses the problem of the conventional encapsulated structures which are only applicable to bottom emission devices.

An embodiment of the invention also provides a process for encapsulating a light-emitting device comprising,
preparing a light-emitting device to be encapsulated; and
forming a protective layer of a quaternary ammonium salt on a top electrode of the light-emitting device, the quaternary ammonium salt having the following structure:

wherein the anion $X^-$ is $Cl^-$, $Br^-$, $I^-$ or $NO_3^-$; and
the substituents $R_1$, $R_2$, and $R_3$ are the same or different.

Furthermore, the encapsulating process further comprising, disposing a encapsulating cover above the protective layer of the quaternary ammonium salt; and fixing the encapsulating cover to the substrate of the light-emitting device.

For example, the fixing the encapsulating cover to the substrate of the light-emitting device comprises, applying a frame sealant to edges for encapsulation on the encapsulating cover and the substrate of the light-emitting device; and curing the frame sealant at the edges for encapsulation.

The encapsulated structure and encapsulating process of the light-emitting device according to an embodiment of the invention can be performed using a light-emitting device to be encapsulated which had been prepared in advance, or can be performed as follows.

Figure 4:
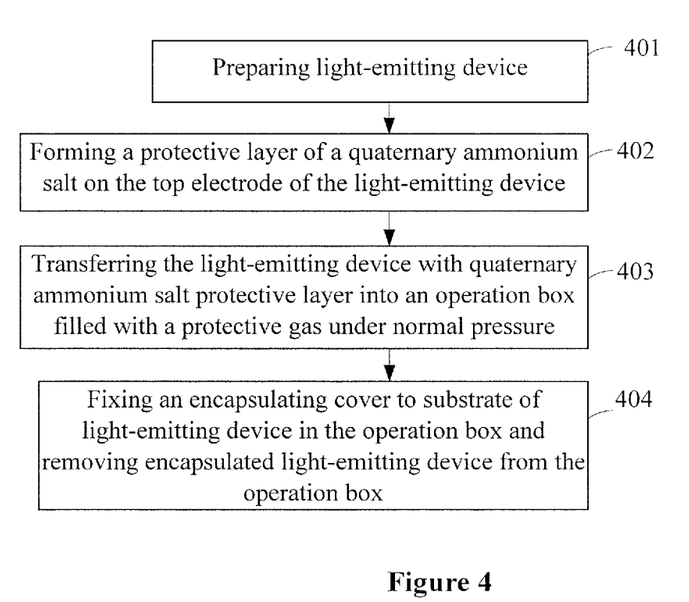
FIG. 4 is a flow chart of the process for encapsulating the organic electroluminescence device of the embodiment of the invention.

As shown in FIG. 4, the process for encapsulating the light-emitting device specifically comprises, Step 401: preparing a light-emitting device comprising a top electrode.

Step 402: forming a protective layer of a quaternary ammonium salt on the top electrode of the light-emitting device, the quaternary ammonium salt having the following structure:

wherein the anion $X^-$ is $Cl^-$, $Br^-$, $I^-$ or $NO_3^-$; and the substituents $R_1$, $R_2$, and $R_3$ are the same or different.

For example, the protective layer of the quaternary ammonium salt may be formed by coating a layer of a quaternary ammonium solution on the top electrode of the light-emitting device with spin coating under vacuum conditions. Alternatively, the protective layer of the quaternary ammonium salt may be formed on the top electrode of the light-emitting device by processes such as sputtering, spray coating, and the like. Solvents useful for dissolving the quaternary ammonium salt may include tetrahydrofuran, benzene, cholorobenzene, or nitrobenzene.

Step 403: The light-emitting device with the protective layer of the quaternary ammonium salt formed is transferred into an operation box filled with a protective gas under normal pressure;

For example, the operation box may be a glove box filled with a protective gas under normal pressure.

Step 404: In the operation box, the encapsulating cover is fixed to the substrate of the light-emitting device, and then the light-emitting device is removed from the operation box.

The process for encapsulating the light-emitting device according to the embodiment of the invention comprises coating a layer of a quaternary ammonium salt on the top electrode of the light-emitting device as the device protective layer, and then pressing a transparent encapsulating cover with a frame sealant attached onto the substrate of the light-emitting device. The protective layer of the quaternary ammonium salt can form a compact self-assembled film on the metal cathode of the organic electroluminescence device. The anion at one side of the film can bind tightly to the metal via electrostatic force, and the hydrophobic moiety at the other side can block the invasion of water and oxygen, and protect the device from any damage caused by friction. Therefore, the embodiment of the invention overcomes the disadvantages of the prior encapsulating process including complicated operational procedure, long curing time, and high cost, and the like, has the advantages of simple operation, short curing time, low cost, and good barrier property to oxygen and moisture, and allows the encapsulation of an OLED top emission device.

Below, the encapsulating process and encapsulated structure of the light-emitting device according to the embodiment of the invention are illustrated in details with a top emission organic electroluminescence device as an example.

FIG. 2 is a schematic diagram of an organic electroluminescence device. As shown in FIG. 2, the organic electroluminescence device comprises a substrate 1, on surface of which an anode layer 2, a hole injection layer 3, a hole transporting layer 4, an organic light-emitting layer 5, an electron transporting layer 6, an electron injection layer 7 and a cathode layer 8 are successively stacked from bottom to top.

The substrate 1 may be a glass substrate or a flexible substrate made of a compound such as polyester or polyimide. The anode layer 2 may be made from an inorganic material or an organic conductive polymer, the inorganic material being a metal oxide such as indium tin oxide, zinc oxide, tin zinc oxide, and the like, or a high work function metal such as gold, copper, silver, and the like, and the organic conductive polymer being polythiophene, sodium polyvinyl benzenesulfonate, or polyaniline. The hole injection layer 3 may be formed from copper phthalocyanine (CuPc) or star polyamines such as 2-TNATA (4,4',4''-tris[2-naphthyl(phenyl)amino]triphenylamine). The hole transporting layer 4 may be formed from a triarylamine material, such as NPB (N,N'-di-(1-naphthyl)-N,N'-diphenyl-1,1-biphenyl-4,4-diamine). The organic light-emitting layer 5 may be formed from a small molecular material, such as a doped fluorescent material or phosphorescent material, preferably MADN (2-methyl-9,10-dinaphthylanthracene), ADN (9,10-dinaphthylanthracene), TBPe (2,5,8,11-tetra-tert-butyl-perylene), $Alq_3$ (aluminum tris(8-hydroxyquinoline)), $Gaq_3$ (gallium tris(8-hydroxyquinoline)), Ga (Saph-q) (gallium (III) (salicylidene-o-aminophenol)-(8-hydroxyquinoline)), Rubrene, DCJTB (4-(dicyanomethylene)-2-tert-butyl-6-(1,1,7,7-tetramethyljulolidin-4-vinyl)-4H-pyran), $Ir(PPy)_3$ (iridium tris (2-phenylpyridine)), or CBP (4,4'-N,N'-dicarbazolylbiphenyl). The electron transporting layer 6 may be formed from an organometallic complex, such as $Alq_3$ (aluminum tris(8-hydroxyquinoline)), gallium tris(8-hydroxyquinoline), gallium (III) (salicylidene-o-aminophenol)-(8-hydroxyquinoline), or from an o-phenanthroline, such as 4,7-diphenyl-1,10-phenanthroline. The electron injection layer 7 may be prepared from an organic electron injection material by way of vapor deposition, and the thickness of the electron injection layer 7 may be from 1 to 10 nm. The cathode layer 8 may be made of a low work function metal, such as lithium (Li), magnesium (Mg), calcium (Ca), strontium (Sr), aluminum (Al), indium (In), and the like, or from an alloy formed from one of them and copper (Cu), gold (Au) or silver (Ag), such as Mg:Ag alloy.

The process for preparing a top emission organic electroluminescence device comprises the steps of:

1) ultrasonically treating the substrate 1 coated with an anode material in a washing agent, rinsing it with a deionized water, ultrasonically de-oiling in an acetone:ethanol mixed solvent (in any ratio), baking under clean conditions until water is completely removed, irradiating with an ultraviolet cleaner for 10-15 minutes, and bombarding the surface of the substrate using low energy cation beam;

2) disposing the substrate 1 with the anode layer 2 in a vacuum chamber at $1 \times 10^{-5}$-$9 \times 10^{-3}$ Pa, vapor depositing on the anode layer a hole injection layer 3 with a thickness of 12-18 nm followed by a hole transporting layer 4 at a rate of 0.1-0.2 nm/s to produce a vapor deposited film having a thickness of 50-70 nm;

3) vapor depositing an organic light-emitting layer 5 on the hole transporting layer 4 at a rate of 0.1-0.2 nm/s, wherein the material forming the organic light-emitting layer 5 may be selected from the group consisting of TBPe:MADN (MADM comprising 2% by weight; thickness: 30 nm), CBP:Ir(PPy)$_3$ (Ir(PPy)$_3$ comprising 7% by weight; thickness: 30 nm), or Alq$_3$:Rubrene:DCJTB (Rubrene comprising 1.5% by weight, DCJTB comprising 3% by weight; thickness: 60 nm);

4) vapor depositing an electron transporting layer 6 on the organic light-emitting layer 5 at a total rate of 0.1-0.2 nm/s to produce a vapor deposited film having a thickness of 20-40 nm;

5) vapor depositing a layer of Liq on the electron transporting layer 6 as an electron injection layer 7 to produce a vapor deposited film having a thickness of 0.5-3 nm;

6) vapor depositing a cathode layer 8 on the aforesaid electron injection layer 7 at a rate of 2.0-3.0 nm/s to produce a vapor deposited film having a thickness of 10-120 nm.

After the preparation of the top emission organic electroluminescence device is complete, it may be encapsulated using the process for encapsulating an organic electroluminescence device according to the embodiment of the invention. The encapsulating process may comprise the steps of:

A. coating a layer of a quaternary ammonium salt onto the top electrode of the top emission organic electroluminescence device in a vacuum chamber, to produce a protective layer having a transmittance of more than 70% in the visible region and a thickness of 1-100 nm;

B. transferring the top emission organic electroluminescence device from the vacuum chamber to a glove box filled with a protective gas under normal pressure, wherein the content of water and oxygen in the protective gas is on an order of magnitude of ppm;

C. placing an encapsulating cover within the glove box;

D. applying a frame sealant (UV glue or other types of epoxy resins) to edges for encapsulation on the encapsulating cover and the glass substrate of the top emission organic electroluminescence device;

E. matching and jointing the edges for encapsulation on both the glass substrate of the top emission organic electroluminescence device and the encapsulating cover;

F. delivering the top emission organic electroluminescence device and the encapsulating cover jointed together to the glove box for curing the frame sealant at the edges for encapsulation, wherein when a UV adhesive is used as the frame sealant, the top emission organic electroluminescence device and the encapsulating cover jointed together are delivered to an ultraviolet exposure device in the glove box to cure the frame sealant at the edges for encapsulation. If a heat curing epoxy resin is used as the frame sealant, the top emission organic electroluminescence device and the encapsulating cover jointed together are delivered to a heat baking device in the glove box to heat-cure the epoxy resin; and H. removing the encapsulated top emission organic electroluminescence device from the glove box upon the completion of encapsulation.

The structure of the quaternary ammonium salt is shown as follows:

wherein the anion $X^-$ is $Cl^-$, $Br^-$, $I^-$ or $NO_3^-$; the substituents $R_1$, $R_2$, and $R_3$ are groups that do not react with the electrode of the cathode layer; $R_1$, $R_2$, and $R_3$ may be the same, or two of them may be the same, or all three are different.

For example, the substituent $R_1$ is selected from the group consisting of substituted alkyl groups having more than 5 carbon atoms, unsubstituted alkyl groups having more than 5 carbon atoms, alkoxyl groups having more than 5 carbon atoms and aralkyl groups having more than 11 carbon atoms;

the substituent $R_2$ is selected from the group consisting of substituted alkyl groups having more than 5 carbon atoms, unsubstituted alkyl groups having more than 5 carbon atoms, alkoxyl groups having more than 5 carbon atoms and aralkyl groups having more than 11 carbon atoms;

and the substituent $R_3$ is selected from the group consisting of substituted alkyl groups having more than 5 carbon atoms, unsubstituted alkyl groups having more than 5 carbon atoms, alkoxyl groups having more than 5 carbon atoms and aralkyl groups having more than 11 carbon atoms.

For example, the number of carbon atoms in $R_1$, $R_2$, and $R_3$ may be the same or close among one another;

wherein, for unsubstituted alkyl groups having more than 5 carbon atoms, for example, the number of carbon atoms may be 5-20; unsubstituted alkyl groups having more than 5 carbon atoms may be selected from the group consisting of n-pentane, n-hexane, n-heptane, n-octane, n-nonane, n-decane, n-undecane, n-dodecane, n-tridecane, n-tetradecane, n-pentadecane, n-hexadecane, n-heptadecane, n-octadecane, n-nonadecane, and n-eicosane;

for substituted alkyl groups having more than 5 carbon atoms, for example, the number of carbon atoms may be 5-20; for example, in the substituted alkyl groups having more than 5 carbon atoms, the substituent is methyl; for example, in the substituted alkyl groups having more than 5 carbon atoms, the substituted position may be at the second or the third carbon atom; the substituted alkyl groups having more than 5 carbon atoms may be selected from the group consisting of 2-methylpentane, 3-methylpentane, 2-methylhexane, 3-methylhexane, 2-methylheptane, 3-methylheptane, 2-methyloctane, 3-methyloctane, 2-methylnonane, 3-methylnonane, 2-methyldecane, 3-methyldecane, 2-methylundecane, 3-methylundecane, 2-methyldodecane, 3-methyldodecane, 2-methyltridecane, 3-methyltridecane, 2-methyltetradecane, 3-methyltetradecane, 2-methylpentadecane, 3-methylpentadecane, 2-methylhexadecane, 3-methylhexadecane, 2-methylheptadecane, 3-methylheptadecane, 2-methyloctadecane, 3-methyloctadecane, 2-methylnonadecane, and 3-methylnonadecane;

the alkoxyl groups having more than 5 carbon atoms are OR', wherein R' is unsubstituted alkyl groups having more than 5 carbon atoms, or substituted alkyl groups having more than 5 carbon atoms; for example, the number of carbon atoms may be 5-20; for example, R' may be the same as the aforesaid unsubstituted alkyl groups having more than 5 carbon atoms and substituted alkyl groups having more than 5 carbon atoms. R' may be selected from the group consisting of n-pentane, n-hexane, n-heptane, n-octane, n-nonane, n-decane, n-undecane, n-dodecane, n-tridecane, n-tetradecane, n-pentadecane, n-hexadecane, n-heptadecane, n-octadecane, n-nonadecane, n-eicosane, 2-methylpentane, 3-methylpentane, 2-methylhexane, 3-methylhexane, 2-methylheptane, 3-methylheptane, 2-methyloctane, 3-methyloctane, 2-methylnonane, 3-methylnonane, 2-methyldecane, 3-methyldecane, 2-methylundecane, 3-methylundecane, 2-methyldodecane, 3-methyldodecane, 2-methyltridecane, 3-methyltridecane, 2-methyltetradecane, 3-methyltetradecane, 2-methylpentadecane, 3-methylpentadecane, 2-methylhexadecane, 3-methylhexadecane, 2-methylheptadecane, 3-methylheptadecane, 2-methyloctadecane, 3-methyloctadecane, 2-methylnonadecane, and 3-methylnonadecane;

the aralkyl groups having more than 11 carbon atoms are $R'C_6H_5$, wherein R' is unsubstituted alkyl groups having more than 5 carbon atoms, or substituted alkyl groups having more than 5 carbon atoms; for example, the number of carbon atoms may be 5-20; for example, R' may be the same as the aforesaid unsubstituted alkyl groups having more than 5 carbon atoms and substituted alkyl groups having more than 5 carbon atoms. R' may be selected from the group consisting of n-pentane, n-hexane, n-heptane, n-octane, n-nonane, n-decane, n-undecane, n-dodecane, n-tridecane, n-tetradecane, n-pentadecane, n-hexadecane, n-heptadecane, n-octadecane, n-nonadecane, n-eicosane, 2-methylpentane, 3-methylpentane, 2-methylhexane, 3-methylhexane, 2-methylheptane, 3-methylheptane, 2-methyloctane, 3-methyloctane, 2-methylnonane, 3-methylnonane, 2-methyldecane, 3-methyldecane, 2-methylundecane, 3-methylundecane, 2-methyldodecane, 3-methyldodecane, 2-methyltridecane, 3-methyltridecane, 2-methyltetradecane, 3-methyltetradecane, 2-methylpentadecane, 3-methylpentadecane, 2-methylhexadecane, 3-methylhexadecane, 2-methylheptadecane, 3-methylheptadecane, 2-methyloctadecane, 3-methyloctadecane, and 2-methylnonadecane, 3-methylnonadecane.

Furthermore, solvents useful for dissolving the quaternary ammonium salt may include tetrahydrofuran, benzene, cholorobenzene, or nitrobenzene.

Figure 3:
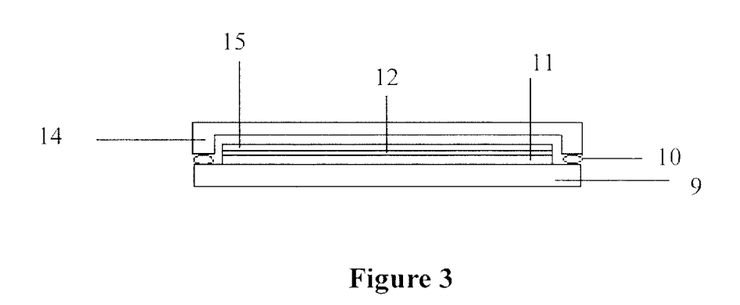
FIG. 3 is a schematic diagram of the components of the encapsulated structure of the organic electroluminescence device of the embodiment of the invention.

After the encapsulating process comprising the aforesaid steps A-H, the organic electroluminescence device obtained has an encapsulated structure as shown in FIG. 3, comprising:

an organic electroluminescence device;

a protective layer of a quaternary ammonium salt 15 formed on the top electrode 12 of the organic electroluminescence device;

an encapsulating cover 14 disposed on the organic electroluminescence device coated with the protective layer of the quaternary ammonium salt 15;

wherein the encapsulating cover is jointed with the substrate of the organic electroluminescence device via a frame sealant 10.

The encapsulated structure of the organic electroluminescence device according to the embodiment of the invention is a structure obtained by coating a layer of quaternary ammonium salt with high transmittance in the visible region on the top electrode of the top emission organic electroluminescence device as the device protective layer, and then pressing a transparent encapsulating cover with a frame sealant attached onto the substrate of the top emission organic electroluminescence device. The protective layer of the quaternary ammonium salt can form a compact self-assembled film on the metal cathode of the organic electroluminescence device. The anion at one side of the film can bind tightly to the metal via electrostatic force, and the hydrophobic moiety at the other side can block the invasion of water and oxygen, and protect the device from any damage caused by friction. Therefore, the embodiment of the invention overcomes the disadvantages of the prior encapsulating process including complicated operational procedure, long curing time, and high cost, and the like, has the advantages of simple operation, short curing time, low cost, and good barrier property to oxygen and moisture, and allows the encapsulation of an OLED top emission device.

The encapsulated structure and process for encapsulating the organic electroluminescence device according to the embodiment of the invention are also applicable to a bottom emission organic electroluminescence device, which comprises to coat a layer of quaternary ammonium salt with high transmittance in the visible region on the top electrode of the light-emitting device as the device protective layer. Compared to the process for manufacturing an encapsulated structure of the top emission organic electroluminescence device, the process for manufacturing an encapsulated structure of the bottom emission organic electroluminescence device further comprises a drying slide 13 and a procedure for making the drying slide 13 (see FIGS. 1 and 2).

For the encapsulated structure of the bottom emission organic electroluminescence device, reference can be made to FIGS. 1 and 2. Specifically, the drying slide 13 is positioned above the protective layer of the quaternary ammonium salt and below the encapsulating cover 14.

The process for encapsulating a bottom emission organic electroluminescence device comprises manufacturing the bottom emission organic electroluminescence device (see FIGS. 1 and 2). The process is shown as follows:

1) forming an ITO electrode layer on a substrate which may be a glass substrate or a flexible substrate made of a compound such as polyester or polyimide; and 2) vapor depositing a light-emitting functional layer (that is, the organic layer 11) and a metal electrode 12 on the ITO glass 9 under vacuum conditions to form the organic electroluminescence device.

After the preparation of the bottom emission organic electroluminescence device is complete, it can be encapsulated using the process for encapsulating an organic electroluminescence device according to the embodiment of the invention. The encapsulating process may comprise the steps of:

A. coating a layer of a quaternary ammonium salt onto the top electrode of the organic electroluminescence device in a vacuum chamber, to produce a protective layer having a transmittance of more than 70% in the visible region and a thickness of 1-100 nm;

B. transferring the organic electroluminescence device from the vacuum chamber to a glove box filled with a protective gas under normal pressure, wherein the content of water and oxygen in the protective gas is on an order of magnitude of ppm;

C. placing an encapsulating cover 14 to which a drying slide 13 is attached within the glove box;

D. applying a frame sealant (UV adhesive or other types of epoxy resins) to edges for encapsulation on the encapsulating cover and the glass substrate of the top emission organic electroluminescence device;

E. matching and jointing the edges for encapsulation on both the glass substrate of the top emission organic electroluminescence device and the encapsulating cover;

F. delivering the top emission organic electroluminescence device and the encapsulating cover jointed together to the glove box for curing the frame sealant at the edges for encapsulation, wherein when an UV adhesive is used as the frame sealant, the top emission organic electroluminescence device and the encapsulating cover jointed together are delivered to an ultraviolet exposure device in the glove box to cure the frame sealant at the edges for encapsulation. If a heat curing epoxy resin is used as the frame sealant, the top emission organic electroluminescence device and the encapsulating cover jointed together are delivered to a heat baking device in the glove box to heat-cure the epoxy resin; and

H. removing the encapsulated organic electroluminescence device from the glove box upon the completion of encapsulation.

The organic electroluminescence device encapsulated according to the embodiment of the invention can be used to manufacture organic transistors, organic integrated circuits, organic solar cells, organic laser, and/or organic sensor.

The encapsulating performance of the top emission organic light-emitting devices according to the embodiment of the invention will be illustrated by way of the following examples. However, the invention is not limited to these examples.

Example 1

The structure of the organic electroluminescence device in the example is shown as follows: the anode layer 2 is ITO; the hole injection layer 3 is made of 2-TNANA, with a thickness of 15 nm; the hole transporting layer 4 is made of NPB, with a thickness of 60 nm; the organic light-emitting layer 5 is made of TBPe:MADN, with a thickness of 30 nm, wherein MADN comprises 2% by weight; the electron transporting layer 6 is made of Alq$_3$, with a thickness of 10 nm; the electron injection layer 7 is made of Liq, with a thickness of 2 nm; the cathode layer 8 is made of MgAg, with a thickness of 10 nm, wherein the weight ratio of Mg:Ag is 10:1; and the protective layer of the quaternary ammonium salt 15 has a thickness of 50 nm. The structure of the quaternary ammonium salt is shown as follows:

The performance indices of the organic electroluminescence device prior to encapsulation are as follows:
Chrominance Coordinates: (X=0.15, Y=0.22);
Threshold Voltage: 4.2V;
Maximum Brightness: 10120 cd/m$^2$ (5V);
Luminous Efficiency: 7.0 cd/A.

The organic electroluminescence device is encapsulated according to the aforementioned encapsulating process. After 30 days, the performance indices of the organic electroluminescence device are as follows:
Chrominance Coordinates: (X=0.15, Y=0.22);
Threshold Voltage: 4.2V;
Maximum Brightness: 10000 cd/m$^2$ (5V);
Luminous Efficiency: 6.9 cd/A.

It can be seen that the change in the light-emitting performance of the organic electroluminescence device is minor.

Comparative Example 1

The structure of the organic electroluminescence device in this comparative example is the same as that in Example 1, except for absence of protective layer of the quaternary ammonium salt, in which:
the anode layer 2 is ITO; the hole injection layer 3 is made of 2-TNANA, with a thickness of 15 nm; the hole transporting layer 4 is made of NPB, with a thickness of 60 nm; the organic light-emitting layer 5 is made of TBPe:MADN, with a thickness of 30 nm, wherein MADN comprises 2% by weight; the electron transporting layer 6 is made of Alq$_3$, with a thickness of 10 nm; the electron injection layer 7 is made of Liq, with a thickness of 2 nm; the cathode layer 8 is made of MgAg, with a thickness of 10 nm, wherein the weight ratio of Mg:Ag is 10:1.

The performance indices of the organic electroluminescence device prior to encapsulation are as follows:
Chrominance Coordinates: (X=0.15, Y=0.22);
Threshold Voltage: 4.2V;
Maximum Brightness: 10100 cd/m$^2$ (5V);
Luminous Efficiency: 7.0 cd/A.

The organic electroluminescence device is encapsulated only with a glass cover. After 30 days, the performance indices of the organic electroluminescence device are as follows:
Chrominance Coordinates: (X=0.15, Y=0.22);
Threshold Voltage: 7.2V;
Maximum Brightness: 4400 cd/m$^2$ (5V);
Luminous Efficiency: 4.0 cd/A.

It can be seen that the light-emitting performance of the organic electroluminescence device of comparative example 1 deteriorates as compared to the device of Example 1.

Example 2

The structure of the organic electroluminescence device in the example is shown as follows: the anode layer 2 is ITO; the hole injection layer 3 is made of 2-TNANA with a thickness of 15 nm; the hole transporting layer 4 is made of NPB with a thickness of 60 nm; the organic light-emitting layer 5 is made of TBPe:MADN with a thickness of 30 nm, wherein MADN comprises 2% by weight; the electron transporting layer 6 is made of Alq$_3$ with a thickness of 30 nm; the electron injection layer 7 is made of Liq with a thickness of 2 nm; the cathode layer 8 is made of MgAg with a thickness of 10 nm, wherein the weight ratio of Mg:Ag is 10:1; and the protective layer of the quaternary ammonium salt 15 has a thickness of 60 nm. The structure of the quaternary ammonium salt is shown as follows:

The performance indices of the organic electroluminescence device prior to encapsulation are as follows:
Chrominance Coordinates: (X=0.15, Y=0.21);
Threshold Voltage: 4.5V;
Maximum Brightness: 13120 cd/m$^2$ (12V);
Luminous Efficiency: 7.5 cd/A.

The organic electroluminescence device is encapsulated according to the aforementioned encapsulating process. After 30 days, the performance indices of the organic electroluminescence device are as follows:
Chrominance Coordinates: (X=0.15, Y=0.21);
Threshold Voltage: 4.7V;
Maximum Brightness: 12000 cd/m² (5V);
Luminous Efficiency: 7.3 cd/A.

It can be seen that the change in the light-emitting performance of the organic electroluminescence device is minor.

Example 3

The structure of the organic electroluminescence device in the example is shown as follows: the anode layer 2 is ITO; the hole injection layer 3 is made of 2-TNANA with a thickness of 15 nm; the hole transporting layer 4 is made of NPB with a thickness of 60 nm; the organic light-emitting layer 5 is made of TBPe:MADN with a thickness of 30 nm, wherein MADN comprises 2% by weight; the electron transporting layer 6 is made of Alq$_3$ with a thickness of 30 nm; the electron injection layer 7 is made of Liq with a thickness of 2 nm; the cathode layer 8 is made of MgAg with a thickness of 10 nm, wherein the weight ratio of Mg:Ag is 10:1; and the protective layer of the quaternary ammonium salt 15 has a thickness of 40 nm. The structure of the quaternary ammonium salt is shown as follows:

The performance indices of the organic electroluminescence device prior to encapsulation are as follows:
Chrominance Coordinates: (X=0.14, Y=0.22);
Threshold Voltage: 3.8V;
Maximum Brightness: 13050 cd/m² (5V);
Luminous Efficiency: 7.8 cd/A.

The organic electroluminescence device is encapsulated according to the aforementioned encapsulating process. After 30 days, the performance indices of the organic electroluminescence device are as follows:
Chrominance Coordinates: (X=0.14, Y=0.22);
Threshold Voltage: 3.9V;
Maximum Brightness: 12050 cd/m² (5V);
Luminous Efficiency: 7.5 cd/A.

It can be seen that the change in the light-emitting performance of the organic electroluminescence device is minor.

Example 4

The structure of the organic electroluminescence device in the example is shown as follows: the anode layer 2 is ITO; the hole injection layer 3 is made of 2-TNANA with a thickness of 15 nm; the hole transporting layer 4 is made of NPB with a thickness of 60 nm; the organic light-emitting layer 5 is made of CBP:Ir(PPy)$_3$ with a thickness of 30 nm, wherein Ir(PPy)$_3$ comprises 7% by weight; the electron transporting layer 6 is made of Alq$_3$ with a thickness of 30 nm; the electron injection layer 7 is made of Liq with a thickness of 2 nm; the cathode layer 8 is made of MgAg with a thickness of 10 nm, wherein the weight ratio of Mg:Ag is 10:1; and the protective layer of the quaternary ammonium salt 15 has a thickness of 30 nm. The structure of the quaternary ammonium salt is shown as follows:

The performance indices of the organic electroluminescence device prior to encapsulation are as follows:
Chrominance Coordinates: (X=0.32, Y=0.64);
Threshold Voltage: 3.0V;
Maximum Brightness: 20500 cd/m² (6V);
Luminous Efficiency: 96 cd/A.

The organic electroluminescence device is encapsulated according to the aforementioned encapsulating process. After 30 days, the performance indices of the organic electroluminescence device are as follows:
Chrominance Coordinates: (X=0.32, Y=0.64);
Threshold Voltage: 3.0V;
Maximum Brightness: 20000 cd/m² (6V);
Luminous Efficiency: 95.5 cd/A.

It can be seen that the change in the light-emitting performance of the organic electroluminescence device is minor.

Example 5

The structure of the organic electroluminescence device in the example is shown as follows: the anode layer 2 is ITO; the hole injection layer 3 is made of 2-TNANA with a thickness of 15 nm; the hole transporting layer 4 is made of NPB with a thickness of 60 nm; the organic light-emitting layer 5 is made of CBP:Ir(PPy)$_3$ with a thickness of 30 nm, wherein Ir(PPy)$_3$ comprises 7% by weight; the electron transporting layer 6 is made of Alq$_3$ with a thickness of 30 nm; the electron injection layer 7 is made of Liq with a thickness of 2 nm; the cathode layer 8 is made of MgAg with a thickness of 10 nm, wherein the weight ratio of Mg:Ag is 10:1; and the protective layer of the quaternary ammonium salt 15 has a thickness of 40 nm. The structure of the quaternary ammonium salt is shown as follows:

The performance indices of the organic electroluminescence device prior to encapsulation are as follows:

Chrominance Coordinates: (X=0.32, Y=0.64);

Threshold Voltage: 3.0V;

Maximum Brightness: 27500 cd/m² (6V);

Luminous Efficiency: 102 cd/A.

The organic electroluminescence device is encapsulated according to the aforementioned encapsulating process. After 30 days, the performance indices of the organic electroluminescence device are as follows:

Chrominance Coordinates: (X=0.32, Y=0.64);

Threshold Voltage: 3.0V;

Maximum Brightness: 25000 cd/m² (6V);

Luminous Efficiency: 98 cd/A.

It can be seen that the change in the light-emitting performance of the organic electroluminescence device is minor.

Example 6

The structure of the organic electroluminescence device in the example is shown as follows: the anode layer 2 is ITO; the hole injection layer 3 is made of 2-TNANA with a thickness of 15 nm; the hole transporting layer 4 is made of NPB with a thickness of 60 nm; the organic light-emitting layer 5 is made of CBP:Ir(PPy)₃ with a thickness of 30 nm, wherein Ir(PPy)₃ comprises 7% by weight; the electron transporting layer 6 is made of Alq₃ with a thickness of 30 nm; the electron injection layer 7 is made of Liq with a thickness of 2 nm; the cathode layer 8 is made of MgAg with a thickness of 10 nm, wherein the weight ratio of Mg:Ag is 10:1; and the protective layer of the quaternary ammonium salt 15 has a thickness of 30 nm. The structure of the quaternary ammonium salt is shown as follows:

The performance indices of the organic electroluminescence device prior to encapsulation are as follows:

Chrominance Coordinates: (X=0.32, Y=0.64);

Threshold Voltage: 3.5V;

Maximum Brightness: 23500 cd/m² (6V);

Luminous Efficiency: 94 cd/A.

The organic electroluminescence device is encapsulated according to the aforementioned encapsulating process. After 30 days, the performance indices of the organic electroluminescence device are as follows:

Chrominance Coordinates: (X=0.32, Y=0.64);

Threshold Voltage: 3.0V;

Maximum Brightness: 20000 cd/m² (6V);

Luminous Efficiency: 90 cd/A.

It can be seen that the change in the light-emitting performance of the organic electroluminescence device is minor.

Example 7

The structure of the organic electroluminescence device in the example is shown as follows: the anode layer 2 is ITO; the hole injection layer 3 is made of 2-TNANA with a thickness of 15 nm; the hole transporting layer 4 is made of NPB with a thickness of 60 nm; the organic light-emitting layer 5 is made of Alq₃:Rubrene:DCJTB with a thickness of 60 nm, wherein Rubrene comprises 1.5% by weight and DCJTB comprises 3% by weight; the electron transporting layer 6 is made of Alq₃ with a thickness of 30 nm; the electron injection layer 7 is made of Liq with a thickness of 2 nm; the cathode layer 8 is made of MgAg with a thickness of 10 nm, wherein the weight ratio of Mg:Ag is 10:1; and the protective layer of the quaternary ammonium salt 15 has a thickness of 20 nm.

The structure of the quaternary ammonium salt is shown as follows:

The performance indices of the organic electroluminescence device prior to encapsulation are as follows:

Chrominance Coordinates: (X=0.63, Y=0.34);
Threshold Voltage: 4.0V;
Maximum Brightness: 10000 cd/m$^2$ (5V);
Luminous Efficiency: 8 cd/A.

The organic electroluminescence device is encapsulated according to the aforementioned encapsulating process. After 30 days, the performance indices of the organic electroluminescence device are as follows:

Chrominance Coordinates: (X=0.63, Y=0.34);
Threshold Voltage: 4.0V;
Maximum Brightness: 9800 cd/m$^2$ (5V);
Luminous Efficiency: 7.9 cd/A.

It can be seen that the change in the light-emitting performance of the organic electroluminescence device is minor.

It should appreciate that in the aforesaid examples, because Cl$^-$, Br$^-$, and I$^-$ are all halide ions and share close chemical properties, a substituent suitable for the quaternary ammonium salt structure with one halide ion is also suitable for the quaternary ammonium salt structure with other halide ions. For example, a substituent suitable for the Cl$^-$ quaternary ammonium salt structure is also suitable for Br$^-$ or I$^-$ quaternary ammonium salt structures, and vice versa.

Example 8

The structure of the organic electroluminescence device in the example is shown as follows: the anode layer 2 is ITO; the hole injection layer 3 is made of 2-TNANA with a thickness of 15 nm; the hole transporting layer 4 is made of NPB with a thickness of 60 nm; the organic light-emitting layer 5 is made of Alq$_3$:Rubrene:DCJTB with a thickness of 60 nm, wherein Rubrene comprises 1.5% by weight and DCJTB comprises 3% by weight; the electron transporting layer 6 is made of Alq$_3$ with a thickness of 30 nm; the electron injection layer 7 is made of Liq with a thickness of 2 nm; the cathode layer 8 is made of MgAg with a thickness of 10 nm, wherein the weight ratio of Mg:Ag is 10:1; and the protective layer of the quaternary ammonium salt 15 has a thickness of 20 nm.

The structure of the quaternary ammonium salt is shown as follows:

The performance indices of the organic electroluminescence device prior to encapsulation are as follows:

Chrominance Coordinates: (X=0.63, Y=0.34);
Threshold Voltage: 3.8V;
Maximum Brightness: 12000 cd/m$^2$ (5V);
Luminous Efficiency: 8.2 cd/A.

The organic electroluminescence device is encapsulated according to the aforementioned encapsulating process. After 30 days, the performance indices of the organic electroluminescence device are as follows:

Chrominance Coordinates: (X=0.63, Y=0.34);
Threshold Voltage: 4.0V;
Maximum Brightness: 11500 cd/m$^2$ (5V);
Luminous Efficiency: 8.0 cd/A.

It can be seen that the change in the light-emitting performance of the organic electroluminescence device is minor.

Example 9

The structure of the organic electroluminescence device in the example is shown as follows: the anode layer 2 is ITO; the hole injection layer 3 is made of 2-TNANA with a thickness of 15 nm; the hole transporting layer 4 is made of NPB with a thickness of 60 nm; the organic light-emitting layer 5 is made of Alq$_3$:Rubrene:DCJTB with a thickness of 60 nm, wherein Rubrene comprises 1.5% by weight and DCJTB comprises 3% by weight; the electron transporting layer 6 is made of Alq$_3$ with a thickness of 30 nm; the electron injection layer 7 is made of Liq with a thickness of 2 nm; the cathode layer 8 is made of MgAg with a thickness of 10 nm, wherein the weight ratio of Mg:Ag is 10:1; and the protective layer of the quaternary ammonium salt 15 has a thickness of 20 nm. The structure of the quaternary ammonium salt is shown as follows:

The performance indices of the organic electroluminescence device prior to encapsulation are as follows:
Chrominance Coordinates: (X=0.63, Y=0.34);
Threshold Voltage: 4.5V;
Maximum Brightness: 15000 cd/m² (5V);
Luminous Efficiency: 9 cd/A.

The organic electroluminescence device is encapsulated according to the aforementioned encapsulating process. After 30 days, the performance indices of the organic electroluminescence device are as follows:
Chrominance Coordinates: (X=0.63, Y=0.34);
Threshold Voltage: 4.7V;
Maximum Brightness: 13000 cd/m² (5V);
Luminous Efficiency: 8.5 cd/A.

It can be seen that the change in the light-emitting performance of the organic electroluminescence device is minor.

It should appreciate that in the aforesaid examples, because $Cl^-$, $Br^-$, and $I^-$ are all halide ions and share close chemical properties, a substituent suitable for the quaternary ammonium salt structure with one halide ion is also suitable for the quaternary ammonium salt structure with other halide ions. For example, a substituent suitable for the $Cl^-$ quaternary ammonium salt structure is also suitable for $Br^-$ or $I^-$ quaternary ammonium salt structures, and vice versa.

It should appreciate that since $NO_3^-$ quaternary ammonium salt is similar to halide ion quaternary ammonium salts, such as $Cl^-$, $Br^-$, and $I^-$ quaternary ammonium salts, they can similarly bind tightly to a metal via electrostatic force to form a compact self-assembled film on the metal cathode of the device, thereby preventing the invasion of water and oxygen into the organic electroluminescence device. Therefore, a substituent suitable for quaternary ammonium salt structure with any halide ion is also suitable for quaternary ammonium salt structure with $NO_3^-$ ion, and vice versa.

From the aforesaid example, it can be seen that after encapsulating the organic electroluminescence device through the process for encapsulating an organic electroluminescence device according to the invention, the resulting protective layer of the quaternary ammonium salt can form a compact self-assembled film on the metal cathode of the device. The anion at one side of the film can bind tightly to the metal via electrostatic force, and the hydrophobic moiety at the other side can block the invasion of water and oxygen, so as to ensure the performance of the organic electroluminescence device.

In the examples of various methods according to the invention, the numberings for the steps are not intended to limit the order of performing various steps. To a person of ordinary skill in the art, modification to the order of the steps, without resorting to inventive work, will fall into the scope of the invention.

The preferable embodiments of the invention are described above. It should understand that a person of ordinary skill in the art can make improvements and modifications without departing from the principle of the invention, and these improvements and modifications should be considered within the scope of the invention.

The invention claimed is:

1. An encapsulated structure of a light-emitting device, comprising:
  a light-emitting device; and
  a protective layer of a quaternary ammonium salt formed on a top electrode of the light-emitting device,
  wherein the quaternary ammonium salt has the following structure:

$$R_2-\overset{\overset{\displaystyle R_1}{|}}{\underset{\underset{\displaystyle R_3}{|}}{N^+}}X^-$$

wherein the anion $X^-$ is $Cl^-$, $Br^-$, $I^-$ or $NO_3^-$; and the substituents $R_1$, $R_2$, and $R_3$ are the same or different.

2. The encapsulated structure according to claim 1, wherein,
  the substituent $R_1$ is selected from the group consisting of substituted alkyl groups having more than 5 carbon atoms, unsubstituted alkyl groups having more than 5 carbon atoms, alkoxyl groups having more than 5 carbon atoms and aralkyl groups having more than 11 carbon atoms; the substituent $R_2$ is selected from the group consisting of substituted alkyl groups having more than 5 carbon atoms, unsubstituted alkyl groups having more than 5 carbon atoms, alkoxyl groups having more than 5 carbon atoms and aralkyl groups having more than 11 carbon atoms; the substituent $R_3$ is selected from the group consisting of substituted alkyl groups having more than 5 carbon atoms, unsubstituted alkyl groups having more than 5 carbon atoms, alkoxyl groups having more than 5 carbon atoms and aralkyl groups having more than 11 carbon atoms.

3. The encapsulated structure according to claim 2, wherein,
  the substituents $R_1$, $R_2$, and $R_3$ are independently selected from the group consisting of substituted alkyl groups having 5-20 carbon atoms, unsubstituted alkyl groups having 5-20 carbon atoms, alkoxyl groups having 5-20 carbon atoms and aralkyl groups having 11-26 carbon atoms.

4. The encapsulated structure according to claim 3, wherein
  the unsubstituted alkyl groups having 5-20 carbon atoms are selected from the group consisting of n-pentane, n-hexane, n-heptane, n-octane, n-nonane, n-decane, n-undecane, n-dodecane, n-tridecane, n-tetradecane, n-pentadecane, n-hexadecane, n-heptadecane, n-octadecane, n-nonadecane, and n-eicosane;
  the substituted alkyl groups having 5-20 carbon atoms are selected from the group consisting of 2-methylpentane, 3-methylpentane, 2-methylhexane, 3-methylhexane, 2-methylheptane, 3-methylheptane, 2-methyloctane, 3-methyloctane, 2-methylnonane, 3-methylnonane, 2-methyldecane, 3-methyldecane, 2-methylundecane, 3-methylundecane, 2-methyldodecane, 3-methyldodecane, 2-methyltridecane, 3-methyltridecane, 2-methyltetradecane, 3-methyltetradecane, 2-methylpentadecane, 3-methylpentadecane, 2-methylhexadecane, 3-methylhexadecane, 2-methylheptadecane, 3-methylheptadecane, 2-methyloctadecane, 3-methyloctadecane, 2-methylnonadecane, and 3-methylnonadecane;

the alkoxyl groups having 5-20 carbon atoms are OR', wherein R' is selected from the group consisting of n-pentane, n-hexane, n-heptane, n-octane, n-nonane, n-decane, n-undecane, n-dodecane, n-tridecane, n-tetradecane, n-pentadecane, n-hexadecane, n-heptadecane, n-octadecane, n-nonadecane, n-eicosane, 2-methylpentane, 3-methylpentane, 2-methylhexane, 3-methylhexane, 2-methylheptane, 3-methylheptane, 2-methyloctane, 3-methyloctane, 2-methylnonane, 3-methylnonane, 2-methyldecane, 3-methyldecane, 2-methylundecane, 3-methylundecane, 2-methyldodecane, 3-methyldodecane, 2-methyltridecane, 3-methyltridecane, 2-methyltetradecane, 3-methyltetradecane, 2-methylpentadecane, 3-methylpentadecane, 2-methylhexadecane, 2-methyloctadecane, 3-methyloctadecane, 2-methylnonadecane, and 3-methylnonadecane;

the aralkyl groups having 11-26 carbon atoms are R'C$_6$H$_5$, wherein R' is selected from the group consisting of n-pentane, n-hexane, n-heptane, n-octane, n-nonane, n-decane, n-undecane, n-dodecane, n-tridecane, n-tetradecane, n-pentadecane, n-hexadecane, n-heptadecane, n-octadecane, n-nonadecane, n-eicosane, 2-methylpentane, 3-methylpentane, 2-methylhexane, 3-methylhexane, 2-methylheptane, 3-methylheptane, 2-methyloctane, 3-methyloctane, 2-methylnonane, 3-methylnonane, 2-methyldecane, 3-methyldecane, 2-methylundecane, 3-methylundecane, 2-methyldodecane, 3-methyldodecane, 2-methyltridecane, 3-methyltridecane, 2-methyltetradecane, 3-methyltetradecane, 2-methylpentadecane, 3-methylpentadecane, 2-methylhexadecane, 3-methylhexadecane, 2-methylheptadecane, 3-methylheptadecane, 2-methyloctadecane, 3-methyloctadecane, 2-methylnonadecane, and 3-methylnonadecane.

5. The encapsulated structure according to claim 1, further comprising,
an encapsulating cover disposed above the protective layer of the quaternary ammonium salt;
the light-emitting device further comprises a substrate,
wherein the encapsulating cover is fixed to the substrate of the light-emitting device with a frame sealant.

6. The encapsulated structure according to claim 1, wherein the protective layer of the quaternary ammonium salt has a light transmittance of no less than 70%.

7. The encapsulated structure according to claim 1, wherein the thickness of the protective layer of the quaternary ammonium salt has a thickness of 1 to 100 nm.

8. A display device comprising the encapsulated structure of the light-emitting device according to claim 1.

9. A process for encapsulating a light-emitting device comprising,
preparing a light-emitting device to be encapsulated; and
forming a protective layer of a quaternary ammonium salt on a top electrode of the light-emitting device, the quaternary ammonium salt having the following structure:

wherein the anion X$^-$ is Cl$^-$, Br$^-$, I$^-$ or NO$_3^-$; and the substituents R$_1$, R$_2$, and R$_3$ are the same or different.

10. The process for encapsulating a light-emitting device according to claim 9, the light-emitting device further comprising a substrate, wherein the process further comprises,
disposing an encapsulating cover above the protective layer of the quaternary ammonium salt; and
fixing the encapsulating cover to the substrate of the light-emitting device.

11. The process for encapsulating a light-emitting device according to claim 10, wherein the fixing the encapsulating cover to the substrate of the light-emitting device comprises,
applying a frame sealant to edges for encapsulation on the encapsulating cover and the substrate of the light-emitting device; and
curing the frame sealant at the edges.

* * * * *